(12) United States Patent
Snyder

(10) Patent No.: US 6,808,492 B2
(45) Date of Patent: Oct. 26, 2004

(54) ENDOSCOPIC CANNULA FIXATION SYSTEM

(75) Inventor: Stephen J. Snyder, Encino, CA (US)

(73) Assignee: Linvatec Corporation, Largo, FL (US)

( * ) Notice: Subject to any disclaimer, the term of this patent is extended or adjusted under 35 U.S.C. 154(b) by 95 days.

(21) Appl. No.: 10/222,524

(22) Filed: Aug. 16, 2002

(65) Prior Publication Data

US 2004/0034364 A1 Feb. 19, 2004

(51) Int. Cl.$^7$ ................................................. A61B 1/04
(52) U.S. Cl. ........................................ 600/114; 600/115
(58) Field of Search .............................. 600/114, 115, 600/201, 204; 604/264, 167, 278, 285, 256, 321, 336

(56) References Cited

U.S. PATENT DOCUMENTS 4,633,865 A * 1/1987 Hengstberger et al. ..... 606/201
5,569,159 A * 10/1996 Anderson et al. ........... 600/114
5,941,815 A * 8/1999 Chang ......................... 600/114
6,589,264 B1 * 7/2003 Barbut et al. ............... 606/200
2002/0147385 A1 * 10/2002 Butler et al. ................. 600/114

* cited by examiner

Primary Examiner—Beverly M. Flanagan

(57) ABSTRACT

A cannula fixation system that allows for easy insertion and removal. A flexible sleeve with corrugations and proximal flange is attached distally to the cannula. The flange serves as a splashguard and a finger retention device. The corrugations have a variable diameter depending upon the tension applied to the proximal flange. The flange is pulled proximally to reduce the diameter of the corrugations for insertion of the cannula. Upon release of the flange, the corrugations expand because of the inherent resiliency of the sleeve to seal against the portal in the patient. The cannula body can be shifted with the sleeve remaining in sealing contact with the portal.

20 Claims, 1 Drawing Sheet

ENDOSCOPIC CANNULA FIXATION SYSTEM

BACKGROUND OF THE INVENTION

1. Field of the Invention

The field of this invention relates to cannulas through which surgical instruments are inserted and more particularly to fixation devices to hold the cannula in one or more positions with respect to the incision in the patient.

2. Description of the Prior Art

Endoscopic surgical procedures involve insertion of instruments through incisions or punctures as well as the placement of the scope and associated light source through other incisions or punctures. During such procedures, a variety of instruments are used through one or more cannulas for access to different locations. As a result, the cannula through which the instruments are inserted and manipulated must be shifted to gain better access to the specific location. Additionally, in arthroscopic procedures (a subset of the category of endoscopic procedures), to allow better viewing of the surgical site, the site is kept under a slight liquid flow pressure to facilitate access and to keep body fluids from occluding the scope. For this reason it is advantageous to maintain a seal between the cannula and the body even if the cannula position requires shifting. Allowing the seal to be broken can result in fluids escaping and hitting the surgeon. Apart from a need to have the option of repositioning the cannula after fixation, another objective of the cannula should be simple and reliable insertion or removal. These benefits are found in the present invention of the cannula fixation system.

Fixation devices have been used in the past on catheters. The purpose of these devices has been to hold the catheter in position, after setting, for the duration of the procedure. An example of a urinary catheter with a corrugated expanding sleeve is shown in U.S. Pat. No. 3,970,090 (Loiacono). This device is intended to be retained in a tubular passageway and, like all catheters is not open at the end to accept surgical instruments. Other examples of passageway catheters with multifold sleeves are U.S. Pat. Nos. 5,827,304 (Hart) and 6,254,571 (Hart). These two patents show the use of the sleeve to remove occlusive material from a body passage. There are patents showing cannulas with dual fold or dual element sleeves, such as U.S. Pat. Nos. 5,122,122 (Allgood) and 5,836,913 (Orth et al.) although these devices are difficult to use and not adjustable.

The following U.S. patents show slots forming strips that expand on compression to anchor but not to seal cannulas or catheters: U.S. Pat. No. 1,621,159 (Evans); U.S. Pat. No. 3,108,595 (Overment); U.S. Pat. No. 3,261,357 (Roberts et al.); U.S. Pat. No. 3,896,804 (Ekbladh et al.); U.S. Pat. No. 3,938,530 (Santomieri); U.S. Pat. No. 4,043,338 (Homm et al.); U.S. Pat. No. 4,608,965 (Anspach et al.); U.S. Pat. No. 4,699,611 (Bowden) and U.S. Pat. No. 5,053,009 (Herzberg). Some patents use spirally cut strips instead of longitudinally oriented strips such as GB 955,490 (Brooke) and U.S. Pat. No. 5,275,975 (Foshee). Yet other US designs involve inflatable fixation devices, such as: U.S. Pat. No. 3,915,171 (Shermeta); U.S. Pat. No. 3,952,742 (Taylor); U.S. Pat. No. 4,077,412 (Moossun); U.S. Pat. No. 4,861,334 (Nawaz); U.S. Pat. No. 5,002,557 (Hasson) and U.S. Pat. No. 5,147,316 (Castillenti). Other US designs employ collet fingers to anchor, such as: U.S. Pat. No. 3,039,468 (Price); U.S. Pat. No. 3,717,151 (Collett) and U.S. Pat. No. 5,445,615 (Yoon). Finally of general interest in the areas of fixation devices for catheters or cannulas are U.S. Pat. No. 4,655,752 (Honkanen et al.)(cannula body with fixed annular ribs); U.S. Pat. No. 5,009,643 (Reich et al.) (threaded cannula body) and U.S. Pat. No. 5,234,455 (Mulhollan) (cannula with distal annular radially extending lip).

None of the foregoing prior art devices have all the benefits afforded by the present invention which presents a cannula that is easily inserted or removed and whose position can be easily altered while it remains sealingly in contact with the incision in the patient. (The term "incision" will be understood to mean any portal through which the cannula is inserted, regardless of how the portal was created.) These and other advantages and aspects of the present invention will be more readily appreciated by those skilled in the art from a review of the description of the preferred embodiment and the claims which appear below.

Accordingly, it is an object of this invention to produce a cannula fixation system enabling a user to, with one hand, place a cannula into a portal, secure it within the portal and subsequently adjust the cannula position and re-secure it.

It is also an object of this invention to produce a cannula fixation system which sealingly secures a cannula in a portal while enabling adjustments of the cannula position within the portal without destroying the seal.

SUMMARY OF THE INVENTION

These and other objects of this invention are achieved by the preferred embodiment disclosed herein which is a cannula which features a fixation system that allows for easy insertion and removal. A flexible sleeve with corrugations and a proximal flange is slidably attached to the cannula. The distal end of the sleeve is fixedly attached near the distal end of the cannula, while the proximal end of the sleeve remains unattached. The flange serves as a splashguard and a finger retention device. The flange is pulled distally to stretch the sleeve and thereby reduce the outer diameter of the corrugations for insertion or movement of the sleeve. Upon release of the flange, the corrugations expand thereby creating a seal against the tissue surrounding the portal in the patient. The cannula body can be shifted longitudinally relative to the sleeve without destroying the sealing contact between the sleeve and the portal.

DETAILED DESCRIPTION OF THE DRAWINGS

DETAILED DESCRIPTION OF THE PREFERRED EMBODIMENT

Figure 1:
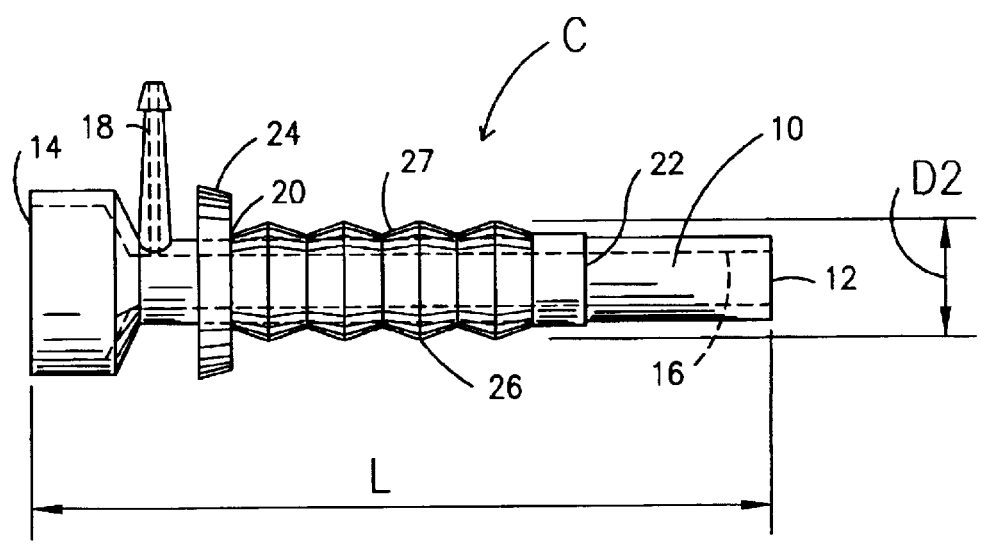
FIG. 1 is a perspective view of the cannula ready for insertion or removal.
Figure 2:
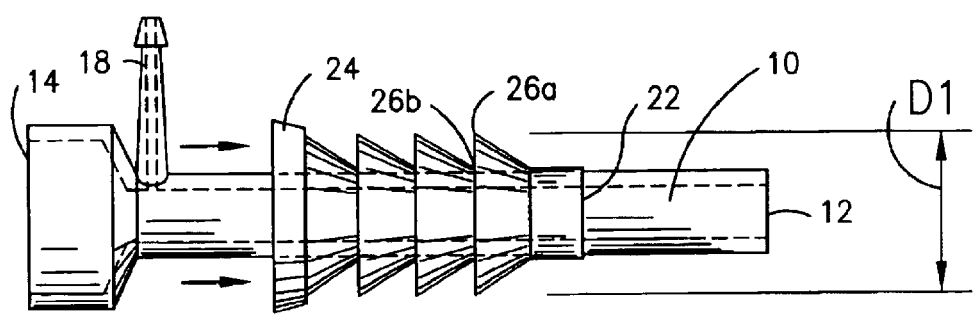
FIG. 2 is the view of FIG. 1 showing the cannula in a deployed state.

Referring to FIGS. 1 and 2, the cannula C has a tubular body 10 having a distal end 12 and a proximal end 14. It has an axial passage 16 that extends from the proximal end 14 to the distal end 12. Lateral passage 18 extends into passage 16 for connection of a vacuum (or fluid) source, in a known manner. Corrugated sleeve 20 is attached at its distal end 22 to body 10. This connection can be fixed or adjustable but in the preferred embodiment is preferably fixed. Fixation can be achieved with an adhesive or with ultrasonic welding or other suitable means. The point of attachment is not shown to scale relative to the proximal and distal ends of cannula C. In the preferred embodiment a cannula with an axial passage diameter of approximately 1 cm would have a length L on the order of 8–9 cm for shoulder arthroscopic procedures and the sleeve distal end would then be attached approximately 1 cm away from the cannula distal end 12. Other sizes of cannulas may be produced for other procedures with appropriate adjustments in sleeve size and placement. The purpose of the connection of the distal end 22 to body 10 is to enable motion of the corrugations of sleeve 20 relative to the cannula to thereby alter the diameter of sleeve 20. Thus, the point of attachment of end 22 could vary along the length of body 10 and could be adjustable. Once selected, however, the end 22 should be secured to body 10 sufficiently to enable sleeve 20 to be stretched and compressed as will be understood below.

The sleeve 20 may be color coded for the size of the passage 16 in the body 10. At its proximal end it has an annular flange 24, which serves as a finger grip and splashguard. Flange 24 has an internal diameter large enough to accommodate body 10, so that the flange can easily slide along the body, and an outer diameter sufficient to enable it to serve as a grasping element and a splash shield. Between its distal end at 22 and flange 24, sleeve 20 is provided with corrugations 26 having ridges 26a and grooves 26b. Sleeve 20 is made of a resilient material such that ridges 26a have a normal, unbiased outer diameter D1 (best seen in FIG. 2). Flange 24 may be pulled proximally to stretch the sleeve to thereby decrease the outer diameter of ridges 26a to diameter D2, the position shown in FIG. 1, for insertion or removal of the cannula C. The ridges decrease in diameter when the flange 24 is pulled toward proximal end 14 because sleeve 20 is attached to the body 10 at 22. The individual ridges along the length of sleeve 20 may have equal or varying outer diameters and can be tapered or have a larger diameter between the ends of sleeve 20 than at the ends. The outer surface 27 of sleeve 20 can be textured to promote gripping and sealing. The inner diameter of the grooves 26b is variable as the sleeve is stretched, but should always allow the sleeve proximal end to slide relative to the cannula body.

The cannula body 10 is preferably a plastic material of sufficient column strength so that it does not kink or buckle during insertion or use. The sleeve 20 is preferably rubber, a resilient elastomeric material or some other biocompatible material with memory so that it goes back to a neutral shape having a larger diameter D1 after the flange 24 is released and the body 10 is in proper position with a portal. Clearly, the portal size must be smaller than diameter D1 to enable the cannula to be "locked" in place. The tendency for the ridges 26a to spring outwardly on release of flange 24 helps to maintain the seal in the portal as well as the position of the body 10. The attachment at 22 is preferably with an adhesive, although other types of fixed or movable attachments are contemplated. The shape, size and number of corrugations 26 can be varied according to the sealing and fixation needs for the size of the opening or passage 16 in cannula C. Similarly the resiliency and flexibility of the material of sleeve 20, and the design (thickness, etc.) of the corrugations may vary depending upon the work site or intended use of the cannula. Various colors can be used for the sleeve 20 consistent with the size of the body 10 or other parameters. Preferably, the flange 24 should extend sufficiently radially outward to make it easy to grip with a fingertip.

Those skilled in the art can see that the cannula C of the present invention has the advantage of being easily inserted and removed. Once cannula C is inserted and the flange 24 is released, ridges 26a expand radially for an anchoring and sealing grip. Thereafter a fluid seal is maintained between the portal and the corrugations of the sleeve. This seal enables the body 10 to be repositioned with respect to the sleeve 20 while the corrugations 26 maintain the anchoring function and the sealing function. That is, cannula C may be shifted inwardly and outwardly without moving the sleeve's point of contact with the portal. The corrugations inherently provide the cannula with the ability to slidably move longitudinally relative to the portal. The ridges and grooves in contact with the portal are held in place by the portal. Any movement of the cannula distal end away from the portal (i.e. pushing the cannula in) will tend to stretch the distal end of the sleeve. That is, the ridges of the corrugations at the distal end will become further apart. Similarly, movement of the cannula distal end toward the portal (i.e. pulling the cannula out) will tend to compress the distal end of the sleeve. Also, the cannula may be tilted relative to the portal axis to allow access to another site without splashing the surgeon because the seal remains intact. This frequently occurs in endoscopic surgery as access to various portions of the work site is necessary during the procedure. To do this the body 10 is simply shifted without a pull force on the flange 24. The shifting can occur in either one of two opposite directions. The flange 24 also serves as a splashguard if the seal in the incision around the corrugations 26 is broken for any reason.

The connection of the sleeve to the cannula may be accomplished without adhesive. For example, the cannula body may be made with a tapered distal end and the sleeve may be made with a fixed diameter, resilient distal end. If the diameter of the sleeve distal end is smaller than the largest diameter of the taper then the sleeve will effectively be fixed to the cannula when the flange is pulled proximally If the sleeve distal end is resilient, it will in effect be secured to the cannula by frictional engagement. In such an embodiment the sleeve could be made separately from the cannula and could be made to fit a variety of cannula sizes.

While corrugations 26 are shown in the preferred embodiment, it will be understood that sleeve 20 could comprise a "smooth" outer surface devoid of ridges and grooves. That is, a sleeve body could be biased so as to be capable of adopting an unbiased, large diameter and a stretched or biased small diameter. Texturing the "smooth" outer surface would facilitate the frictional engagement of the sleeve with the portal. Thus, the term "corrugated" as used herein is intended to encompass such alternatives.

It will be understood by those skilled in the art that numerous improvements and modifications may be made to the preferred embodiment of the invention disclosed herein without departing from the spirit and scope thereof.

What is claimed is:

1. A cannula for selective fixation within a portal for providing instrument access to a surgical work site comprising:
    an elongated body having a passage therethrough sufficiently large for passage of a surgical instrument to the surgical work site;
    a flexible generally cylindrical sleeve coaxially surrounding said body, said sleeve having a distal end and a proximal end, said distal end of said sleeve attached to said body for movement substantially therewith and said proximal end slidable relative to said body, said sleeve able to selectively adopt a first position in which it has a reduced outer diameter when placed in tension and a second position in which it has a larger outer diameter when said tension is removed.

2. The cannula of claim 1 wherein said body is longitudinally movable with respect to said sleeve when tension is removed from said sleeve and it moves toward said larger diameter.

3. The cannula of claim 1 wherein said sleeve has at least one corrugation.

4. The cannula of claim 1 wherein said sleeve has multiple corrugations.

5. The cannula of claim 4 wherein said sleeve further comprises an annular flange adjacent said proximal end thereof.

6. The cannula of claim 5 wherein said corrugations each comprise a large diameter ridge and a small diameter groove and wherein all ridge diameters are equal.

7. The cannula of claim 5 wherein said sleeve has a texture on an outer surface to enhance frictional engagement with a portal.

8. The cannula of claim 5 wherein said corrugations are color-coded to indicate the size of said passage in said body.

9. The cannula of claim 1 wherein said connection is fixed.

10. The cannula of claim 1 wherein said connection is movable.

11. A cannula comprising:
    a body having a passage therethrough large enough to allow insertion of a surgical instrument;
    a flexible device mounted to an outer surface of said body to selectively seal said body to an incision in a patient, said device permitting repositioning of said body while remaining sealed in the incision.

12. The cannula of claim 11 wherein said body has a distal end tapered distally and has, at the proximal end of said taper, a predetermined diameter and wherein said flexible device has a distal end which is resilient with a diameter normally smaller than said predetermined diameter whereby, upon assembly of said flexible device distal end with said tapered distal end, said flexible device will be frictionally engaged with said body.

13. The cannula of claim 12 wherein said flexible device comprises a flange mounted closest to a proximal end thereof.

14. The cannula of claim 13 wherein said flexible device is connected to said body at a distal end of said flexible device.

15. The cannula of claim 14 wherein said flexible device surrounds said body, said flexible device having a reduced diameter when placed in tension and a larger relaxed diameter when said tension is removed.

16. The cannula of claim 15 wherein said flexible device comprises corrugations having a texture on an outer surface to enhance grip.

17. A cannula comprising:
    a body having a passage therethrough sufficiently large for passage of a surgical instrument to a surgical site in a patient;
    a flexible sleeve surrounding and attached at one location to said body, said sleeve having a reduced diameter when placed in tension and a larger diameter when said tension is removed.

18. A method of using a cannula at a portal during an endoscopic surgical procedure comprising the steps of:
    providing a cannula having an axis, a distal end, a proximal end and an axially aligned bore sufficiently large to enable the passage therethrough of a predetermined endoscopic instrument;
    providing a generally cylindrical flexible corrugated sleeve having a distal end, a proximal end and an inner diameter greater than the outer diameter of said cannula, said sleeve having an outer diameter that is selectively adjustable by longitudinal motion of said sleeve proximal end;
    securing said distal end of said flexible corrugated sleeve to the exterior of said cannula and adjacent said distal end of said cannula, for movement substantially therewith;
    providing at said proximal end of said flexible corrugated sleeve a grasping means for enabling a user to grasp said proximal end of said flexible corrugated sleeve and move it longitudinally relative to said cannula;
    moving said proximal end of said flexible corrugated sleeve in a predetermined direction to minimize the outer diameter thereof;
    inserting said cannula with said attached flexible corrugated sleeve into the portal;
    moving said proximal end of said flexible corrugated sleeve to maximize the outer diameter thereof to thereby secure the cannula relative to the portal;
    reciprocating the cannula relative to said flexible corrugated sleeve without moving said sleeve longitudinally relative to said portal to selectively position said distal end of said cannula.

19. A method according to claim 18 comprising: forming said grasping means as an annular flange having an axis aligned with said axis of said cannula.

20. A method according to claim 18 comprising:
    providing said cannula with a distally tapered distal end having a predetermined maximum diameter;
    providing said flexible corrugated sleeve with a resilient distal end having an unbiased diameter less than said maximum diameter of said tapered distal end;
    assembling said sleeve and said cannula with said resilient distal end frictionally engaging said tapered distal end.

* * * * *